United States Patent [19]

Takagi et al.

[11] Patent Number: 5,498,789
[45] Date of Patent: Mar. 12, 1996

[54] METHOD OF PRODUCING AROMATIC CARBONATE

[75] Inventors: Masatoshi Takagi; Hidekazu Miyagi; Yuji Ohgomori; Hiroshi Iwane, all of Inashiki, Japan

[73] Assignee: Mitsubishi Chemical Corporation, Tokyo, Japan

[21] Appl. No.: 348,116

[22] Filed: Nov. 28, 1994

[30] Foreign Application Priority Data

| Jan. 12, 1994 | [JP] | Japan | 6-001715 |
| Jul. 25, 1994 | [JP] | Japan | 6-172695 |
| Aug. 3, 1994 | [JP] | Japan | 6-182601 |

[51] Int. Cl.$^6$ ................................. C07C 69/96
[52] U.S. Cl. .................. 558/270; 558/271; 558/274
[58] Field of Search .......................... 558/270, 271, 558/274

[56] References Cited

U.S. PATENT DOCUMENTS 4,201,721  5/1980  Hallgren .................... 558/270
5,142,086  8/1992  King, Jr. et al. .

Primary Examiner—Jose G. Dees
Assistant Examiner—Dwayne C. Jones
Attorney, Agent, or Firm—Oblon, Spivak, McClelland, Maier & Neustadt

[57] ABSTRACT

The present invention relates to a method of producing an aromatic carbonate by reacting an aromatic hydroxy compound, carbon monoxide and oxygen using a catalyst system for suppressing the production of aryl aromatic o-hydroxycarboxylate as a by-product. The catalyst system consists of the following compounds:

(A) at least one selected from palladium and palladium compounds;

(B) at least one selected from lead compounds; and (C) at least one halide selected from quaternary ammonium halides and quaternary phosphonium halides; and if required, (D) at least one selected from copper and copper compounds.

The method of the present invention can increase the yield of an aromatic carbonate per palladium (the turnover number of palladium).

18 Claims, No Drawings

METHOD OF PRODUCING AROMATIC CARBONATE

BACKGROUND OF THE INVENTION

1. Field of the Invention

The present invention relates to a method of producing an aromatic carbonate using a specified catalyst system. Aromatic carbonates, particularly diphenyl carbonate are useful as raw materials for polycarbonate or the like.

2. Description of the Related Art

A method of reacting an aromatic hydroxy compound with phosgene is generally used for producing an aromatic carbonate. However, this method is undesirable because of the high toxicity of phosgene.

Some methods have thus been proposed which do not use phosgene in which an aromatic carbonate is produced from an aromatic hydroxy compound, carbon monoxide and oxygen.

The catalyst used in such methods can be found in the following. U.S. Pat. No. 4,187,242 discloses a method which uses as a catalyst a palladium compound, a compound containing a metal selected from the group IIIA, IVA, VA, VIA, IB, IIB, VIB or VIIB in the periodic table, and a base. U.S. Pat. No. 4,201,721 discloses a method which uses a palladium compound, a manganese or cobalt complex, a base and a desiccating agent. Japanese Patent Laid-Open No. 1-16555 discloses a method which uses a palladium compound, iodine and zeolite. Japanese Patent Laid-Open No. 2-104564 discloses a method which uses a palladium compound, a divalent or trivalent manganese compound, tetraalkylammonium halide and a quinone. Japanese Patent Laid-Open No. 2-142754 discloses a method which uses a palladium compound, a divalent or trivalent cobalt compound, tetraalkylammonium halide and a quinone. Japanese Patent Laid-Open No. 5-25095 discloses a method which uses palladium or a palladium compound, a cobalt compound, a halide and a basic compound. Japanese Patent Laid-Open No. 5-39247 discloses a method which uses a palladium compound, a copper compound, a quinone and onium halide. Japanese Patent Laid-Open No. 5-58961 discloses a method which uses at least one of palladium and a palladium compound, a cobalt compound and alkali metal halide. U.S. Pat. No. 5,142,086 discloses a method which uses a catalyst system comprising palladium, quaternary ammonium salts, a metallic cocatalyst selected from cobalt, iron, cerium, manganese, molybdenum, samarium, vanadium, chromium and copper; and an organic cocatalyst selected from aromatic ketones, aliphatic ketones and aromatic polycyclic hydrocarbons. Japanese Patent Laid-Open No. 6-9505 discloses a method which uses a palladium compound, a cerium compound, and a quaternary ammonium salt. Japanese Patent Laid-Open No. 6-41020 discloses a method which uses palladium compounds, a metallic cocatalyst selected from manganese, cobalt and copper, and a nitrile compound. U.S. Pat. No. 5,231,210 discloses a method which uses a palladium compound, a cobalt pentacoordinate complex, and a quaternary onium salt. U.S. Pat. No. 5,284,964 discloses a method which uses an inorganic cocatalyst selected from palladium compounds; an inorganic cocatalyst selected from cobalt, manganese and copper; quaternary onium salts and terpyridine.

In the examples described in the above publications, the yield of aromatic carbonate per palladium (turnover number of palladium) is less than 700, and thus the catalyst activity is not always satisfactory.

SUMMARY OF THE INVENTION

As a result of supplementary experiments performed by the inventors using phenol as a substrate and conventional metallic cocatalysts, the use of any of the catalysts produced, as a by-product, o-hydroxyaryl-carboxylic acid aryl ester which is a structural isomer of an aromatic carbonate, in the present case, phenyl salicylate. The isomer is a compound which is very difficult to separate from an aromatic carbonate by distillation or the like.

It is therefore an object of the present invention to provide a method of efficiently producing an aromatic carbonate, which can reduce the amount of by-product produced that is difficult to separate, and which can obtain a large turnover number of palladium.

The inventors found a method of producing an aromatic carbonate by reacting an aromatic hydroxy compound, carbon monoxide and oxygen, that uses a catalyst system consisting of the following compounds:

(A) at least one selected from palladium and palladium compounds;

(B) at least one selected from lead compounds; and (C) at least one halide selected from quaternary ammonium halides and quaternary phosphonium halides.

This method can efficiently produce an aromatic carbonate and suppress the production of o-hydroxyaryl-carboxylic acid aryl ester as a by-product, as compared with conventional catalyst systems. The inventors also unexpectedly found that in the catalyst system of the present invention, the turnover number of palladium is significantly increased by decreasing the amount of palladium used. These findings resulted in the achievement of the present invention.

However, this catalyst system produces a large amount of halogenation product of aromatic hydroxy compounds as a by-product. As a result of examining the suppression of the production of this by-product, it was found that the addition of (D) at least one selected from copper and copper compounds to the above catalyst system can significantly suppress the production of halogenation product of aromatic hydroxy compounds to obtain a more preferable catalyst system. The present invention has been achieved on the basis of this finding.

DETAILED DESCRIPTION OF THE INVENTION

1. Reaction Raw Material (1) Aromatic hydroxy compound

The aromatic hydroxy compound used in the present invention is an aromatic mono- or poly-hydroxy compound. Examples of such hydroxy compounds include phenol: substituted phenols such as cresol, xylenol, trimethylphenol, tetramethylphenol, ethylphenol, propylphenol, methoxyphenol, ethoxyphenol, chlorophenol, dichlorophenol, bromophenol, dibromophenol and isomers thereof; naphthol; substituted naphthols such as methylnaphthol, ethylnaphthol, chloronaphthol, bromonaphthol and isomers thereof; various bisphenols such as 2,2-bis(4-hydroxyphenyl)propane; various biphenols; various heteroaromatic hydroxy compounds and isomers thereof; and alkyl or halogen substitution products of the above compounds. Of these compounds, phenol is most preferred.

(2) Carbon monoxide

The carbon monoxide used in the present invention may be high-purity carbon monoxide or carbon monoxide diluted with another gas such as nitrogen, argon, carbon dioxide or hydrogen, which have no negative effects on the reaction.

(3) Oxygen

The oxygen used in the present invention may be high-purity oxygen, air or oxygen diluted with another gas such as nitrogen, argon, carbon dioxide or hydrogen, which have no negative effects on the reaction.

2. Catalyst

The catalyst used in the reaction of the present invention comprises a combination system containing at least one selected from the compounds exemplified in each of components (A), (B) and (C) below.

(A) Palladium or palladium compound

Examples of palladium or palladium compounds that can be used in the present invention include palladium black; supported palladium such as palladium/carbon, palladium/alumina, palladium/silica and the like; inorganic palladium salts such as palladium chloride, palladium bromide, palladium iodide, palladium sulfate, palladium nitrate and the like; organic palladium salts such as palladium acetate, palladium oxalate and the like. Further, palladium (II) acetylacetonate, a palladium complex compound such as $PdCl_2(PhCN)_2$, $PdCl_2(PPh_3)_2$, $Pd(CO)(PPh_3)_3$, $[Pd(NH_3)_4]Cl_2$, $Pd(C_2H_4)(PPh_3)_2$, $[(3-C_3H_5)PdCl]_2$, $Pd(DBA)_2$, $Pd_2(DBA)_3 \cdot CHCl_3$ [DBA indicates dibenzylideneacetone] in which carbon monoxide, nitril, amine, phosphine or olefin is coordinated around the palladium, or a mixture of palladium and a compound which can produce the above complex compound in the reaction system. Palladium/carbon and palladium acetate are preferred.

The molar ratio of the palladium component to the aromatic hydroxy compound is preferably within the range of $10^{-7}$ to $10^{-2}$, more preferably $10^{-6}$ to $10^{-3}$.

Since, in the catalyst system of the present invention, the turnover number of palladium can be increased by decreasing the amount of palladium used, the use of as a small amount of palladium as possible is preferable from the viewpoint of the cost of the catalyst. However, the use of extremely small amount of palladium deteriorates the yield of the aromatic carbonate based on the aromatic hydroxy compound, and causes difficulties in recovering the aromatic carbonate.

(B) Lead compound

The lead compound used in the present invention is preferably soluble in a liquid phase under reaction conditions. Examples of such lead compounds include lead oxides such as PbO, $Pb_3O_4$, $PbO_2$ and the like; organic acid salts of lead such as $Pb(OAc)_2$, $Pb(OAc)_4$, $Pb(C_2O_4)$, $Pb(OCOC_2H_5)_2$ and the like; inorganic lead salts such as $Pb(NO_3)_2$, $PbSO_4$ and the like; alkoxy and aryloxy lead such as $Pb(OMe)_2$, $Pb(OPh)_2$ and the like; lead complex compounds such as phthalocyanine lead and the like. Of these compounds, lead oxides and lead compounds represented by the formula $Pb(OR)_2$ wherein R indicates an aryl group having a carbon number of 6 to 10, or an acyl group having an alkyl group having a carbon number of 1 to 4, or are preferred.

Although the amount of the lead compound used in reaction is not limited, the molar ratio to the aromatic hydroxy compound is preferably within the range of $10^{-4}$ to $10^{-1}$, more preferably within the range of $10^{-4}$ to $10^{-2}$.

(C) Halide

The halide used in the present invention is a quaternary ammonium halide or quaternary phosphonium halide, which is represented by the following formula:

$R^1R^2R^3R^4NX$ or $R^1R^2R^3R^4PX$ wherein $R^1$ to $R^4$ each indicate an alkyl or aryl group having a carbon number of 1 to 10, $R^1$ to $R^4$ may be the same as or different from each other, and X indicates halogen. Bromides are preferred, for example tetra-n-butylammonium bromide, tetraphenylphosphonium bromide and the like.

Although the amount of the halide used in reaction is not limited, the molar ratio to the aromatic hydroxy compound is preferably within the range of $10^{-4}$ to 1, more preferably within the range of $10^{-3}$ to $10^{-1}$.

A more preferred reaction system, when the component (C) is selected from quaternary ammonium halides, further contains at least one selected from the compounds exemplified as component (D) below.

(D) Copper or copper compounds

The copper or copper compound used in the present invention is a monovalent or divalent copper compound or metallic copper. Examples of such copper or copper compounds include organic acid salts of copper such as $Cu(OAc)_2$; inorganic copper salts such as $Cu(NO_3)_2$, $CuSO_4$ and the like; copper halides such as $CuBr$, $CuBr_2$, $CuCl$, $CuCl_2$ and the like; copper oxides such as $Cu_2O$, $CuO$ and the like; copper complex compounds such as phthalocyanine copper and the like; copper alkoxides such as $Cu(OPh)_2$, $Cu(OMe)_2$ and the like; metallic copper such as copper powder, copper wire and the like. Of these compounds, organic acid salts of copper, copper halides, copper oxides and metallic copper are preferred.

Although the amount of the copper or copper compound used in reaction is not limited, the molar ratio to the aromatic hydroxy compound is preferably within the range of $10^{-4}$ to $10^-$, more preferably within the range of $10^{-4}$ to $10^{-2}$.

3. Reaction Conditions

Reaction is effected in a reactor in which a catalyst consisting of the components (A), (B) and (C), and further, in a more preferred system, component (D), are charged under pressure of carbon monoxide and oxygen and heating.

In the reaction, the absolute total pressure is within the range of 1 to 500 atm, preferably 1 to 150 atm. The composition ratio between carbon monoxide and oxygen is preferably beyond the explosion range of these gases from the viewpoint of safety. The partial pressures of carbon monoxide and oxygen are preferably 30 to 100 arm and 1 to 10 arm, respectively.

The reaction temperature is within the range of 20° to 300° C., preferably 80° to 250° C.

Although the reaction time depends upon reaction conditions, the reaction time is generally several minutes to several hours.

In reaction, an organic additive such as an aromatic diol such as hydroquinone, an oxidation product thereof such as quinone, or amine, all of which are used in conventional catalyst systems, may be added to the reaction system.

An inert solvent such as hexane, heptane, cyclohexane, benzene, toluene, xylene, methylene chloride, chloroform, chlorobenzene, diethyl ether, diphenyl ether, tetrahydrofuran, dioxane or acetonitrile can be used. When an aromatic hydroxy compound as a raw material is used as a reaction solvent, another solvent need not be used.

EXAMPLES

The present invention will be described in detail below with reference to the examples and comparative examples.

Example 1

3.01 g (32 mmol) of phenol, 2.7 mg (0.012 mmol) palladium acetate, 2.8 mg (0.012 mmol) of lead (II) oxide, and 78.1 mg (0.24 mmol) of tetrabutylammonium bromide were charged in a 40-ml Hastelloy autoclave. After the air in the system was replaced by carbon monoxide, 60 atm of carbon monoxide and 30 atm of dry air were introduced into the autoclave, followed by stirring at 100° C. for 3 hours. After reaction, the gaseous and liquid phases were quantitatively analyzed by gas chromatography. As a result, diphenyl carbonate was obtained with a yield of 6.75% (1.08 mmol) based on phenol. Phenyl salicylate, bromophenols and carbon dioxide were produced as by-products in amounts of 0.74% based on the diphenyl carbonate produced, 46.7% (the sum of o- and p-bromophenols, m-bromophenol was not observed) based on the tetrabutylammonium bromide used, and 0.30 mmol, respectively.

Examples 2 to 5

The same reaction as that in Example 1 was effected except that 0.012 mmol each of various lead compounds was used in place of lead oxide. The formula of the lead compounds used, the yield of diphenyl carbonate based on phenol, and the amounts of phenyl salicylate based on the diphenyl carbonate produced, bromophenols based on the tetrabutylammonium bromide used, and carbon dioxide, which were produced as by-products, are shown in Table 1.

TABLE 1

| Example No. | 2 | 3 | 4 | 5 |
|---|---|---|---|---|
| Pb compound (0.012 mmol) | $PbO_2$ | $Pb_3O_4$ | Pb $(OAc)_2$ | Pb $(OPh)_2$ |
| Diphenyl carbonate (%) | 5.93 | 6.22 | 4.54 | 6.51 |
| Phenyl salicylate (%) | 0.84 | 0.76 | 0.88 | 0.74 |
| Bromophenols (%/Br$^-$) | 55.1 | 50.8 | 43.0 | 48.3 |
| Carbon dioxide (mmol) | 0.30 | 0.23 | 0.18 | 0.30 |

Example 6

The same reaction as that in Example 1 was effected except that 25.5 mg (0.012 mmol Pd) of 5%-palladium/carbon was used in place of palladium acetate. As a result, diphenyl carbonate was obtained with a yield of 8.38% (1.33 mmol) based on phenol. Phenyl salicylate, bromophenols and carbon dioxide were produced as by-products in amounts of 0.67% based the on diphenyl carbonate produced, 54.0% (the sum of o- and p-bromophenols, m-bromophenol was not observed) based on the tetrabutylammonium bromide used, and 0.48 mmol, respectively.

Example 7

The same reaction as that in Example 1 was effected except that 100.6 mg (0.24 mmol) of tetraphenylphosphonium bromide was used in place of tetrabutylammonium bromide. As a result, diphenyl carbonate was obtained with a yield of 8.00% (1.29 mmol) based on phenol. Phenyl salicylate, bromophenols and carbon dioxide were produced as by-products in amounts of 0.62% based on the diphenyl carbonate produced, 53.2% (the sum of o- and p-bromophenols, m-bromophenol was not observed) based on the tetraphenylphosphonium bromide used, and 0.46 mmol, respectively.

Example 8

The same operation as that in Example 1 was performed further adding 0.6 mg (0.003 mmol) of copper (II) acetate monohydrate. As a result, diphenyl carbonate was obtained with a yield of 8.28% (1.32 mmol) based on phenol. Phenyl salicylate, bromophenols and carbon dioxide were produced as by-products in amounts of 0.83% based on the diphenyl carbonate produced, 18.3% (the sum of o- and p-bromophenols, m-bromophenol was not observed) based on the tetrabutylammonium bromide used, and 0.38 mmol, respectively. Examples 9 to 13

The same operation as that in Example 8 was performed except that 0.012 mmol each of various copper compounds was used in place of copper (II) acetate monohydrate. The formula of the copper compounds used, the yield of diphenyl carbonate based on phnol and the yields of phenyl salicylate based on the diphenyl carbonate produced, bromophenols based on the tetrabutylammonium bromide used, and carbon dioxide, which were produced as by-products, are shown in Table 2.

TABLE 2

| Example No. | 9 | 10 | 11 | 12 | 13 |
|---|---|---|---|---|---|
| Cu compound (0.012 mmol) | Cu $(acac)_2$ | CuBr | CuO | $Cu_2O$ | Cu powder |
| Diphenyl carbonate (%) | 8.08 | 7.58 | 7.36 | 6.44 | 6.25 |
| Phenyl salicylate (%) | 1.01 | 0.81 | 0.85 | 1.36 | 1.29 |
| Bromophenols (%/Br$^-$) | 19.1 | 17.9 | 17.9 | 13.7 | 12.9 |
| Carbon dioxide (mmol) | 0.22 | 0.22 | 0.19 | 0.16 | 0.13 |

Example 14

The same reaction as that in Example 8 was effected except that 25.5 mg (0.012mmol Pd) of 5%-palladium/carbon was used in place of palladium acetate. As a result, diphenyl carbonate was obtained with a yield of 9.12% (1.46 mmol) based on phenol. Phenyl salicylate, bromophenols and carbon dioxide were produced as by-products in amounts of 0.88% based on the diphenyl carbonate produced, 15.0% (the sum of o- and p-bromophenols, m-bromophenol was not observed) based on the tetrabutylammonium bromide used, and 0.45 mmol, respectively.

Comparative Example 1

The same reaction as that in Example 1 was effected except that 2.9 mg (0.012 mmol) of manganese (II) acetate tetrahydrate was used in place of lead (II) oxide. As a result, diphenyl carbonate was obtained with a yield of 9.05% (1.44 mmol) based on phenol. Phenyl salicylate, bromophenols and carbon dioxide were produced as by-products in amounts of 4.44% based on the diphenyl carbonate produced, 100% (the sum of o- and p-bromophenols, m-bromophenol was not observed) based on the tetrabutylammonium bromide used, and 1.94 mmol, respectively.

Comparative Example 2

The same reaction as that in Example 1 was effected except that 3.0 mg (0.012 mmol) of cobalt (II) acetate tetrahydrate was used in place of lead (II) oxide. As a result, diphenyl carbonate was obtained with a yield of 1.26% (0.20 mmol) based on phenol. Phenyl salicylate and carbon dioxide were produced as by-products in amounts of 9.05% based on the diphenyl carbonate produced, and 0.15 mmol, respectively. The production of bromophenols was not observed.

Comparative Example 3

The same reaction as that in Example 1 was effected except that 4.0 mg (0.012 mmol) of cerium (III) acetate monohydrate was used in place of lead (II) oxide. As a result, diphenyl carbonate was obtained with a yield of 6.02% (0.96 mmol) based on phenol. Phenyl salicylate, bromophenols and carbon dioxide were produced as by-products in amounts of 3.82% based on the diphenyl carbonate produced, 9.9% (the sum of o- and p-bromophenols, m-bromophenol was not observed) based on the tetrabutylammonium bromide used, and 0.18 mmol, respectively.

Comparative Example 4

The same reaction as that in Example 1 was effected except that tetrabutylammonium bromide was not used. As a result, diphenyl carbonate was produced with a yield of no more than 0.50% based on phenol.

Comparative Example 5

The same reaction as that in Example 1 was effected except that 28.6 mg (0.24 mmol) of potassium bromide was used in place of tetrabutylammonium bromide. As a result, diphenyl carbonate was obtained with a yield of 1.54% (0.25 mmol) based on phenol. Phenyl salicylate, bromophenols and carbon dioxide were produced as by-products, in amounts of 2.60% based on the diphenyl carbonate produced, 22.9% (the sum of o- and p-bromophenols, m-bromophenol was not observed) based on tetrabutylammonium bromide used, and 0.18 mmol, respectively.

Example 15

12.23 g (130 mmol) of phenol, 4.26 mg (2.0 μmol Pd) of 5%-palladium/carbon (produced by N. E. Chemcat Co., Ltd.), 10.71 mg (0.048 mmol) of lead (II) oxide, and 322.4 mg (1.0 mmol) of tetrabutylammonium bromide were charged in a 50-ml Hastelloy autoclave. After air in the system was replaced by carbon monoxide, 60 atm of carbon monoxide and 30 atm of dry air were introduced into the autoclave, followed by stirring at 100° C. for 3 hours. After reaction, the gaseous and liquid phases were quantitatively analyzed by gas chromatography. As a result, diphenyl carbonate was obtained with a yield of 4.54% (2.95 mmol, a turnover number of palladium of 1475) based on phenol. Phenyl salicylate, bromophenol and carbon dioxide were produced as by-products in amounts of 0.58% based on the diphenyl carbonate produced, 43.6% (the sum of o- and p-bromophenols, m-bromophenol was not observed) based on the tetrabutylammonium bromide used, and 0.38 mmol, respectively.

Examples 16 to 19

The same reaction as that in Example 15 was effected except that the amounts of 5%-palladium/carbon and tetrabutylammonium bromide used were changed. The amounts palladium/carbon and tetrabutylammonium bromide used, the yield of diphenyl carbonate, the turnover number (TN) of palladium, and the amounts of phenyl salicylate based on the diphenyl carbonate produced, bromophenol based on tetrabutylammonium bromide and carbon dioxide, which were produced as by-products, are shown in Table 3.

TABLE 3

| Example No. | 16 | 17 | 18 | 19 |
| --- | --- | --- | --- | --- |
| Pd/C (μmol) | 2.0 | 2.0 | 1.0 | 0.5 |
| NBu$_4$Br (mmol) | 2.0 | 3.0 | 2.0 | 2.0 |
| Diphenyl carbonate (%) | 9.62 | 10.15 | 6.31 | 2.96 |

TABLE 3-continued

| Example No. | 16 | 17 | 18 | 19 |
| --- | --- | --- | --- | --- |
| Turnover number | 3120 | 3305 | 4100 | 3860 |
| Phenyl salicylate (%) | 0.45 | 0.45 | 0.59 | trace |
| Bromophenols (%/Br$^-$) | 29.3 | 31.4 | 35.8 | 34.6 |
| Carbon dioxide (mmol) | 1.21 | 1.58 | 0.88 | 0.38 |

Example 20

The same operation as that in Example 15 was performed except that 0.45 mg (2.0 mol) of palladium acetate was used in place of 5%-palladium/carbon. As a result, diphenyl carbonate was obtained with a yield of 5.35% (3.48 mmol, a turnover number of palladium of 1740) based on phenol. Phenyl salicylate, bromophenosl and carbon dioxide were produced as by-products in amounts of 0.57% based on the diphenyl carbonate produced, 47.1% (the sum of o- and p-bromophenols, m-bromophenol was not observed) based on tetrabutylammonium bromide used, and 0.38 mmol, respectively.

Example 21

The same reaction as that in Example 15 was effected except that the amount of 5% palladium/carbon is changed to 2.13 mg (1.0 mol Pd) and further adding 9.58 mg (0.048 mmol) of copper (II) acetate monohydrate. As a result, diphenyl carbonate was obtained with a yield of 4.15% (2.70 mmol, a turnover number of palladium of 2455) based on phenol. Phenyl salicylate, bromophenols and carbon dioxide were produced as by-products in amounts of 0.86% based on the diphenyl carbonate produced, 10.8% (the sum of o- and p-bromophenols, m-bromophenol was not observed) based on the tetrabutylammonium bromide used, and 0.36 mmol, respectively.

Comparative Example 6

The same operation as that in Example 15 was performed except that 16.09 mg (0.048 mmol) of cerium (III) acetate monohydrate was used in place of lead oxide. As a result, diphenyl carbonate was obtained with a yield of 2.01% (1.31 mmol, a turnover number of palladium of 690) based on phenol. Phenyl salicylate, bromophenols and carbon dioxide were produced as by-products in amounts of 2.52% based on the diphenyl carbonate produced, 9.1% (the sum of o- and p-bromophenols, m-bromophenol was not observed) based on tetrabutylammonium bromide used, and 0.19 mmol, respectively.

What is claimed is:

1. A method of producing an aromatic carbonate by reacting an aromatic hydroxy compound, carbon monoxide and oxygen, wherein reaction is effected in a reaction system in the presence of catalyst system consisting essentially of:

(A) at least one selected from palladium or palladium compounds;

(B) at least one selected from lead compounds; and (C) at least one halide selected from quaternary ammonium halides or quaternary phosphonium halides.

2. A method according to claim 1, wherein the component (A) is palladium acetate or palladium/carbon.

3. A method according to claim 1, wherein the component (B) is lead oxide or a lead compound represented by the formula Pb(OR)$_2$ wherein R is an aryl group having a carbon number of 6 to 10, or an acyl group having an alkyl group with a carbon number of 1 to 4.

4. A method according to claim 1, wherein the component (C) is a bromide.

5. A method according to claim 4, wherein the component (C) is tetrabutylammonium bromide or tetraphenylphosphonium bromide.

6. A method according to claim 1, wherein the molar ratio of the component (A) to the aromatic hydroxy compound is within the range of $10^{-6}:1$ to $10^{-3}:1$.

7. A method according to claim 1, wherein the molar ratio of the component (B) to the aromatic hydroxy compound is within the range of $10^{-4}:1$ to $10^{-2}:1$.

8. A method according to claim 1, wherein the molar ratio of the component (C) to the aromatic hydroxy compound is within the range of $10^{-3}:1$ to $10^{-1}:1$.

9. A method according to claim 1, wherein the partial pressures of carbon monoxide and oxygen are 30 to 100 atm and 1 to 10 atm, respectively.

10. A method according to claim 1, wherein the component (C) is selected from quaternary ammonium halides.

11. A method according to claim 1, wherein (C) is selected from quaternary ammonium chloride or bromide, or quaternary phosphonium chloride or bromide.

12. A method according to claim 1, wherein the reaction temperature is within the range of 80° to 130° C.

13. A method according to claim 1, wherein the catalyst system consists of (A), (B) and (C).

14. A method according to claim 1, wherein (C) is selected from quaternary ammonium chloride or bromide, or quaternary phosphonium chloride or bromide.

15. A method of producing an aromatic carbonate by reacting an aromatic hydroxy compound, carbon monoxide and oxygen, wherein reaction is effected in a reaction system in the presence of a catalyst system consisting essentially of:

(A) at least one selected from palladium or palladium compounds;

(B) at least one selected from lead compounds;

(C) at least one halide selected from quaternary ammonium halides or quaternary phosphonium halides, and (D) at least one selected from copper or copper compounds.

16. A method according to claim 15, wherein the component (D) is selected from organic acid salts of copper, copper halides, copper oxides and metallic copper.

17. A method according to claim 1, wherein the molar ratio of the component (D) to the aromatic hydroxy compound is within the range of $10^{-4}:1$ to $10^{-2}:1$.

18. A method according to claim 15, wherein the catalyst system consists of (A), (B), (C) and (D).

* * * * *